United States Patent
Kim et al.

(10) Patent No.: US 6,415,014 B1
(45) Date of Patent: Jul. 2, 2002

(54) THREE-DIMENSIONAL IMAGE CONSTRUCTING METHOD USING X-RAY APPARATUS

(75) Inventors: Hyeong-Cheol Kim, Seongnam; Hyoung-Jo Jeon, Yongin; Jae-Hyun Jung, Anyang; Yong-Won Kim; Won Choi, both of Suwon; Kwang-Jun Yoon, Seoul; Hyun-Kwon Jung, Kwangmyong; Jun-Bo Kim, Seoul; Jae-Wan Kim, Taejon; Young-Jun Roh, Taejon; Hyung-Suck Cho, Taejon, all of (KR)

(73) Assignee: Samsung Electronics Co., Ltd., Suwon (KR)

( * ) Notice: Subject to any disclaimer, the term of this patent is extended or adjusted under 35 U.S.C. 154(b) by 0 days.

(21) Appl. No.: 09/966,362

(22) Filed: Oct. 1, 2001

(30) Foreign Application Priority Data

Jul. 6, 2001 (KR) .......................... 2001-40380

(51) Int. Cl.⁷ .............................. A61B 6/03; G01N 23/04
(52) U.S. Cl. .............................. 378/22; 378/4; 378/901
(58) Field of Search ................................ 378/4, 21, 22, 378/901

(56) References Cited

U.S. PATENT DOCUMENTS

| | | | | |
|---|---|---|---|---|
| 4,020,346 A | * | 4/1977 | Dennis | 250/519.1 |
| 6,195,412 B1 | * | 2/2001 | Tobin et al. | 250/363.03 |
| 6,252,933 B1 | | 6/2001 | Artig | 378/121 |

* cited by examiner

Primary Examiner—David V. Bruce
(74) Attorney, Agent, or Firm—Staas & Halsey LLP (57) ABSTRACT

Disclosed herein is a three-dimensional image constructing method using an X-ray apparatus. In the three-dimensional image constructing method, a construction space of a subject and information for the construction space are set. Thereafter, a plurality of transmission images of the subject are obtained. The data of the construction space are calculated on the basis of the information for the construction space set at the setting step and the transmission images obtained at the image obtaining step. The construction space is constructed on the basis of the data calculated at the image processing step.

6 Claims, 7 Drawing Sheets

THREE-DIMENSIONAL IMAGE CONSTRUCTING METHOD USING X-RAY APPARATUS

BACKGROUND OF THE INVENTION

1. Field of the Invention

The present invention relates generally to X-ray apparatuses, and more particularly to a three-dimensional image constructing method using an X-ray apparatus that is used to construct a three-dimensional image from X-ray images.

2. Description of the Prior Art

Figure 1:
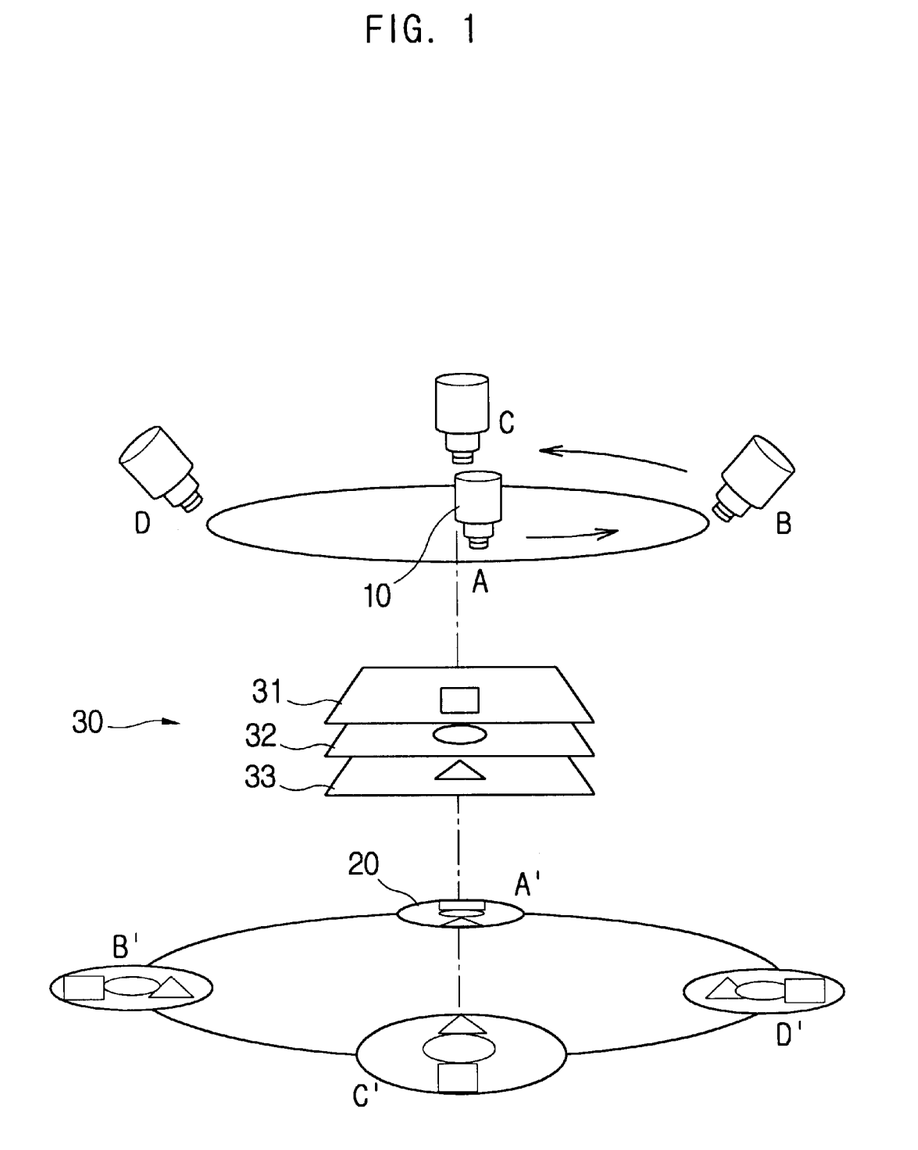
FIG. 1 is a schematic diagram explaining a conventional X-ray apparatus.

FIG. 1 is a schematic diagram explaining a conventional X-ray apparatus.

Referring to FIG. 1, the conventional X-ray apparatus is comprised of an X-ray irradiator 10 for irradiating X-rays and an X-ray detector 20 for detecting X-rays having been transmitted through a subject 30. The X-ray irradiator 10 is operated in conjunction with the X-ray detector 20. That is, as the X-ray irradiator 10 irradiates X-rays to the subject 30 while being rotated, the X-ray detector 20 detects X-rays having been transmitted through the subject 30 while being rotated in conjunction with the X-ray irradiator 10.

Figure 2:
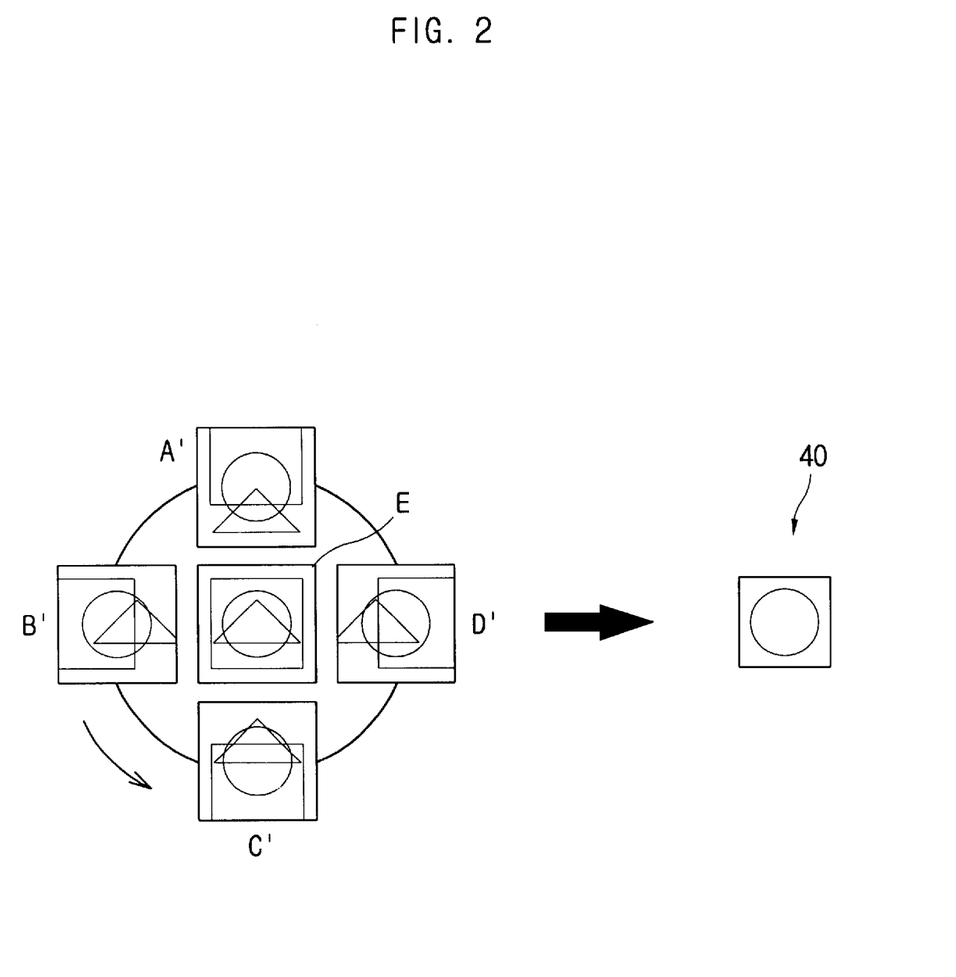
FIG. 2 is a view showing the photographing operation of the conventional X-ray apparatus.

FIG. 2 is a view showing the photographing operation of the conventional X-ray apparatus.

Referring to FIG. 2, while being rotated along a first circular orbit, the X-ray irradiator 10 irradiates X-rays to the subject 30 at positions A, B, C and D positioned on the first circular orbit. At this time, the X-ray detector 20 is rotated in conjunction with the X-ray irradiator 10 along a second circular orbit having the same central axis as the first circular orbit along which the X-ray detector 20 is rotated. Accordingly, the X-ray detector 20 detects X-rays having been transmitted through the subject 30 at positions A', B', C' and D' positioned on the second circular orbit. Images detected by the X-ray detector 20 at the positions A', B', C' and D' are illustrated in FIG. 2.

Thereafter, the conventional X-ray apparatus constructs a target image 40 of a cross section, that is, a desired focal plane 32 by overlapping a plurality of slant transmission images obtained by detecting the X-rays having been transmitted through the subject 30 at positions A', B', C' and D' and a vertical transmission image E.

However, in the conventional X-ray apparatus, a tomogram of a focal plane can be obtained, but there is a problem that it is difficult to obtain a three-dimensional image of a subject. Additionally, the tomogram is obtained while an X-ray irradiator and an X-ray detector are moved in conjunction with each other, so there occur problems that a long period of time is required to obtain the tomogram and the precision of the apparatus is deteriorated.

SUMMARY OF THE INVENTION

Accordingly, the present invention has been made keeping in mind the above problems occurring in the prior art, and an object of the present invention is to provide a three-dimensional image constructing method using an X-ray apparatus, which is capable of constructing a three-dimensional image from X-ray images.

In order to accomplish the above object, the present invention provides a three-dimensional image constructing method using an X-ray apparatus, comprising: a setting step of setting a construction space of a subject and information for the construction space; an image obtaining step of obtaining a plurality of transmission images of the subject; an image processing step of calculating data of the construction space on the basis of the information for the construction space set at the setting step and the transmission images obtained at the image obtaining step; and a constructing step of constructing the construction space on the basis of the data calculated at the image processing step.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Hereinafter, a three-dimensional image construction method using an X-ray apparatus in accordance with the present invention is described in detail with reference to accompanying drawings.

Figure 3:
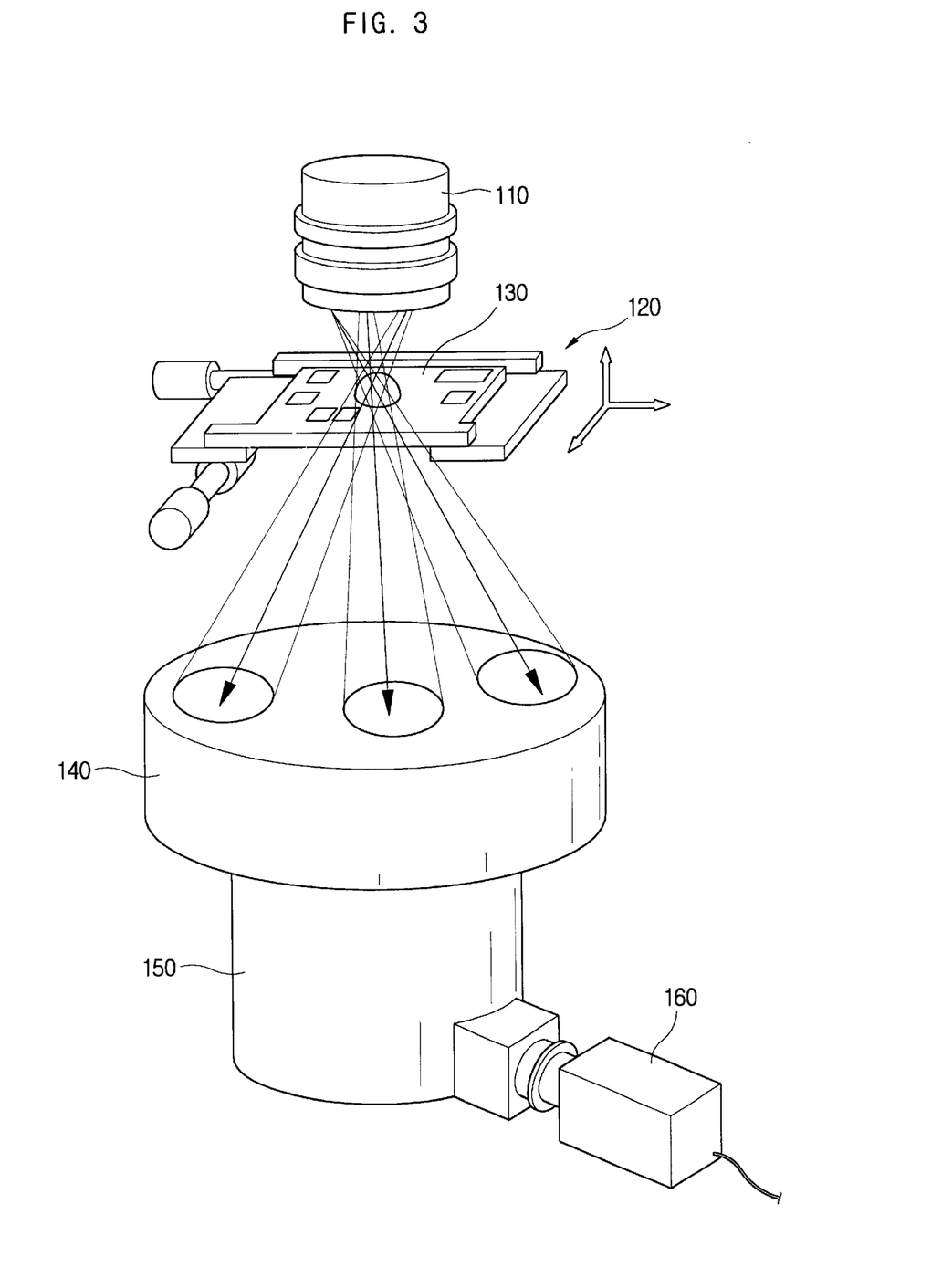
FIG. 3 is a schematic view showing an X-ray apparatus in accordance with the present invention.

FIG. 3 is a schematic view showing an X-ray apparatus in accordance with the present invention.

Referring to FIG. 3, an X-ray apparatus of the present invention is comprised of a table 120, an X-ray irradiator 110 for irradiating X-rays to a subject 130 laid on the table 120, an image multiplier tube 140 for converting X-rays having been transmitted through the subject 130 into a visible ray image, an image selection unit 150 for selecting a specific region from the image multiplied by the image multiplier tube 140, and a photographing unit 160 for obtaining the image of the specific region selected by the image multiplier tube 140.

The X-rays irradiated by the X-ray irradiator 110 are transmitted through the subject laid on the table 120, and formed on the screen of the image multiplier tube 140 in the form of a visible image. Accordingly, the image of the selected region is obtained by the photographing unit 160.

In order to obtain a transmission X-ray image in a different direction with regard to the subject, the position of an X-ray source is changed. When the position of the X-ray source is changed, an image formed with an angle of projection can be obtained. In this case, since the screen of the image multiplier tube 140 is sufficiently large, the X-ray image of the subject can be formed on the image multiplier tube 140 in spite of a change in the position of the X-ray source.

Figure 4:
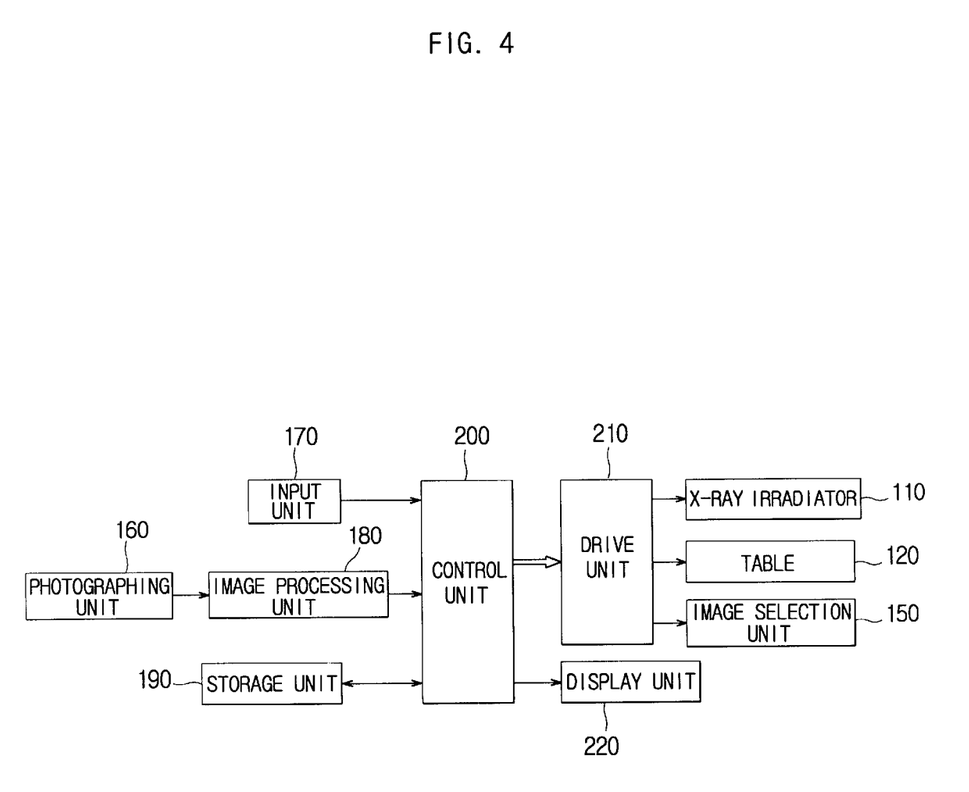
FIG. 4 is a block diagram showing the construction of the X-ray apparatus of the present invention in more detail.

FIG. 4 is a block diagram showing the construction of the X-ray apparatus of the present invention in more detail.

Referring to FIG. 4, in more detail, the X-ray apparatus of the present invention is comprised of a control unit 200 for controlling the entire operation of the apparatus, an input unit for receiving information from a user and transmitting it to the control unit 200, the X-ray irradiator 110 for irradiating X-rays to the subject 130, the table 120 for supporting the subject 130, the image selection unit 150 for selecting a specific region from an image formed on the image multiplier tube 140 by X-rays irradiated from the X-ray irradiator 110, a drive unit 210 for driving the image selection unit 150, the photographing unit 160 for photographing the specific region of the image selected by the image selection unit 150, and an image processing unit 180 for processing an image photographed by the photographing unit 160 and transmitting it to the control unit 200.

In addition, the X-ray apparatus of the present invention further includes a storage unit 190 for storing image data according to the control of the control unit 200 and a display unit 220 for displaying a processed image according to the control of the control unit 200.

Figure 5:
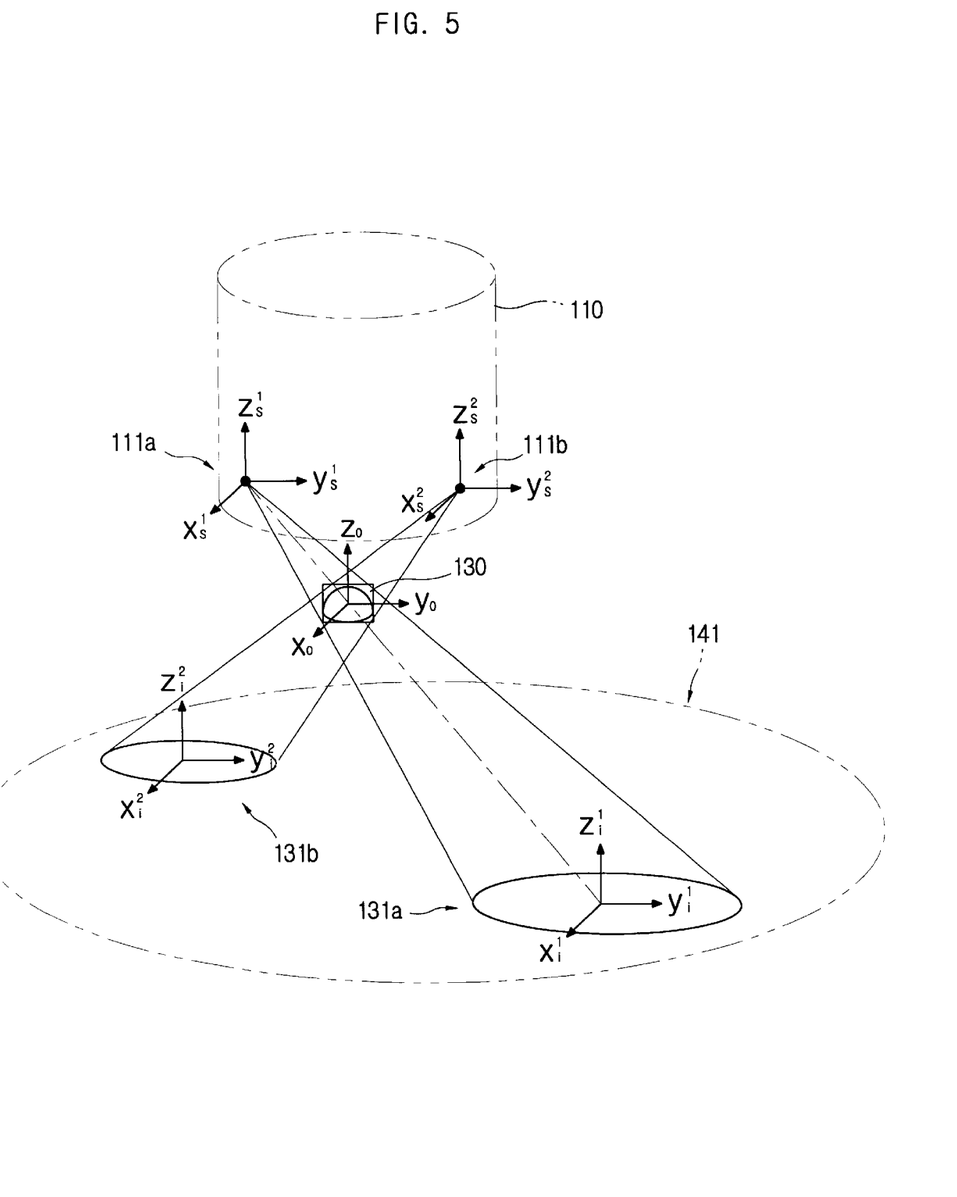
FIG. 5 is a view showing the operation of irradiating X-rays to a subject by the X-ray apparatus of the present invention.

FIG. 5 is a view showing the operation of irradiating X-rays to a subject by the X-ray apparatus of the present invention.

An X-ray irradiated from a first position 111*a* of the X-ray irradiator 110 is transmitted through the subject 130, and formed on the image multiplier tube 140 as a first image 131*a*. Another X-ray irradiated from a second position 111*b* of the X-ray irradiator 110 different from the first position 111*a* is transmitted through the subject 130, and formed on the screen 141 of the image multiplier tube 140 as a second image 131*b*.

When an X-ray is transmitted through the subject 130 as described above, the X-ray is attenuated in the process of passing through the subject 130. The image multiplier tube 140 obtains an X-ray image by converting the intensity of the X-ray attenuated in the process of passing through the subject 130 into the brightness value of an image.

Figure 6:
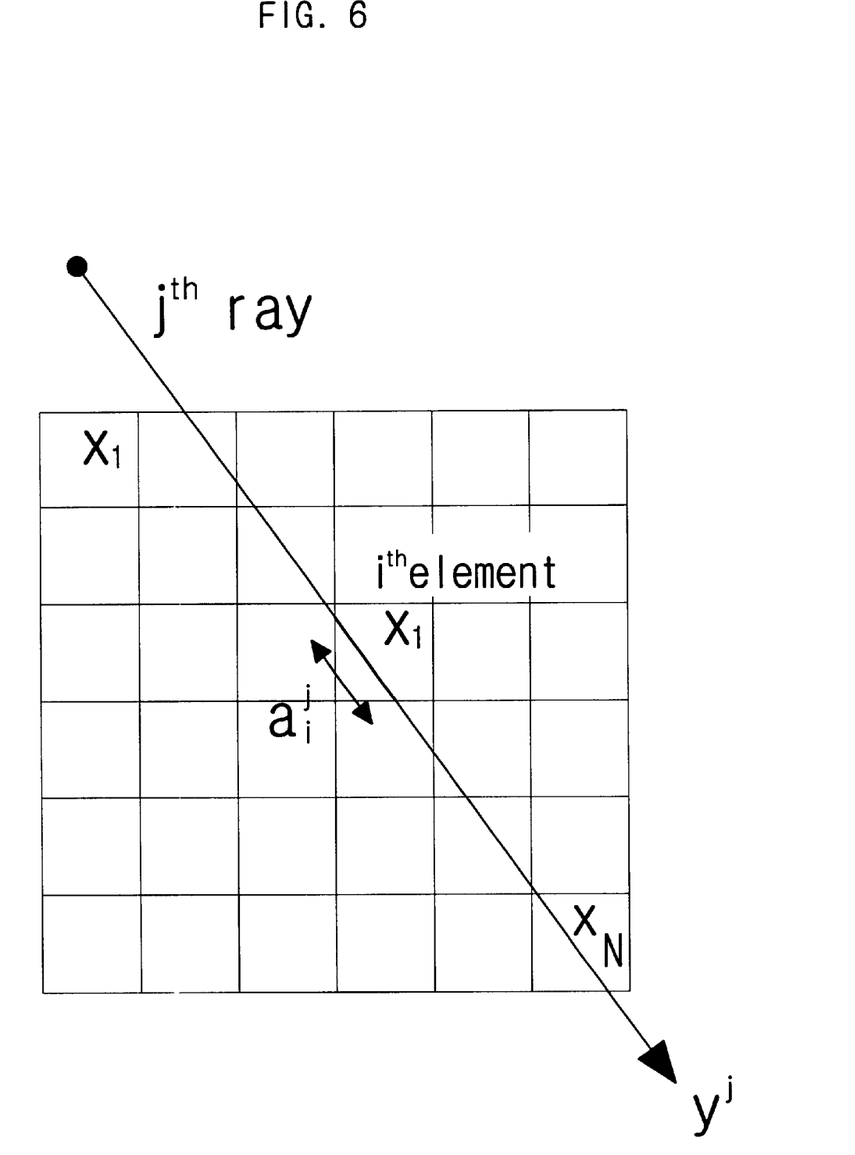
FIG. 6 is a view showing a X-ray projection model in accordance with the present invention.

The degree of attenuation of an X-ray is dependent on the physical properties of the subject 130. The intensity of the X-ray having been transmitted through the subject 130 can be represented as the following equation 1:

Equation 1

$$I = I_0 e^{-\mu x} = I_0 e^{-(\mu/\rho)\rho x}$$

where x=the thickness of a subject through which an X-ray is transmitted, $I_0$=the intensity of an X-ray irradiated, I=the intensity of an X-ray having been transmitted through a subject, $\mu$=a linear attenuation coefficient, and $\mu/\rho$=a mass absorption coefficient FIG. 6 is a view showing an X-ray projection model.

In the three-dimensional image constructing method of the present invention, a generalized subject formed of a random medium can be modeled by dividing the subject into a plurality of lattice elements (hereinafter, referred to as voxels) having the same interval and assigning density values to these voxels.

As indicated by equation 1, the degree of attenuation occurring while an X-ray is transmitted through a subject is dependent on the density of the subject, that is, a medium, or the transmission distance of the X-ray. From the transmission characteristics of the X-ray, the degree of attenuation of an X-ray being transmitted through a plurality of media can be modeled in the form of a linear combination of the densities of the media and the transmission distance of the X-ray.

Accordingly, as indicated in FIG. 6, when a jth X-ray transmitted through a construction space represented by a plurality of voxels is transmitted through an ith voxel and forms a transmission image y, a density value x can be defined using a distance a by the jth X-ray is transmitted through a ith voxel of the construction space. In this case, a transmission image $y^j$ for the jth X-ray can be represented as the following equation 2.

Equation 2

$$y^j = \sum_{i=1}^{N} a_i^j \cdot x_i$$

where i=an index for a voxel of a construction space, j=an index for an X-ray, a=a distance by which a jth X-ray is transmitted through an ith voxel, and $x_i$=a density value of an ith voxel.

If the above-described equation 2 is converted to an equation for all the X-rays concerned with all the projection directions, the following equation 3 can be obtained in the form of a matrix.

Equation 3

$$Y = Ax,$$

and $$A = \begin{bmatrix} a_1^1 & a_2^1 & \cdots & a_N^1 \\ a_1^2 & a_2^2 & \cdots & a_N^2 \\ \cdots & \cdots & \cdots & \cdots \\ a_1^M & a_2^M & \cdots & a_N^M \end{bmatrix} = \begin{bmatrix} a^1 \\ a^2 \\ \cdots \\ a^M \end{bmatrix}$$

where M=the number of X-rays, and N=the number of voxels.

A three-dimensional image can be constructed by calculating density values and the transmission distances of X-rays for all the voxels by the above-described equation 3 and applying these data to all the voxels.

Figure 7:
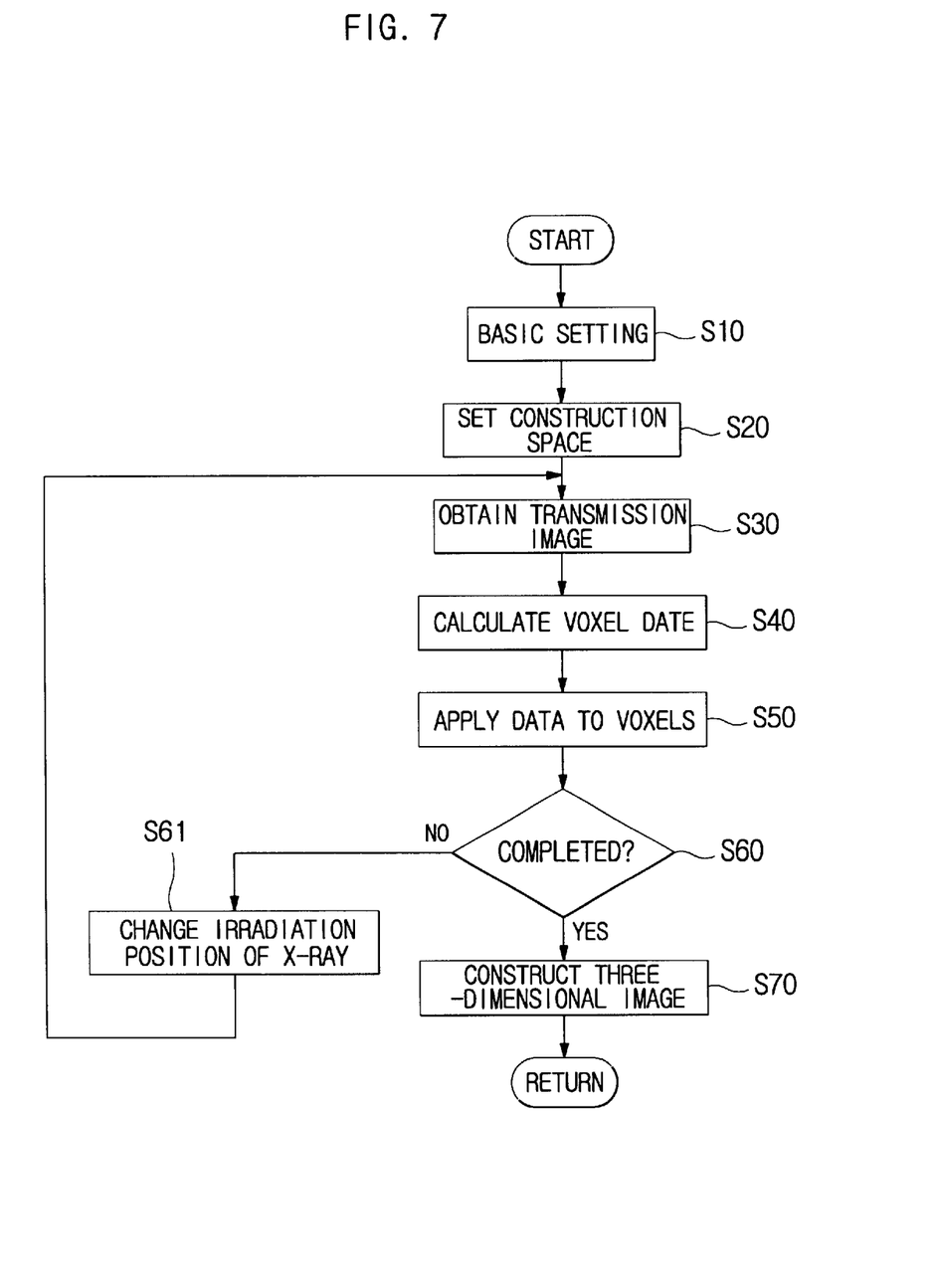
FIG. 7 is a flowchart showing the three-dimensional image constructing method of the present invention.

FIG. 7 is a flowchart showing the three-dimensional image constructing method of the present invention.

Referring to FIG. 7, first of all, the positional relation between the X-ray irradiator 110 for irradiating X-rays to the subject 130 (that is, an irradiation position) and an image formed on the image multiplier tube 140 is set (S10). Subsequently, a construction space of the subject 130 desired to construct is set (S20).

Thereafter, an image of the subject 130 is obtained. In order to obtain the image of the subject 130, the control unit 200 sets a desired position by controlling the table 120. Additionally, the control unit 200 controls the drive unit 210 so as to cause X-rays to be irradiated to the subject 130 from the X-ray irradiator 110.

Accordingly, an image is formed on the image multiplier tube 140. The control unit 200 selects a specific region from the image by the image selection unit 150, and photographs the specific region selected by the photographing unit 160. A transmission image taken by the photographing unit 160 is sent to the control unit 200 through the image processing unit 180, and, thereby, the control unit 200 obtains the transmission image (S30) and stores the obtained transmission image in the storage unit 190.

After the transmission image is obtained, the control unit 20 calculates space densities of all the voxels of a construction space of the subject 130, and stores the space densities in the storage unit 190 (S40). The control unit 200 sets the space densities at the preset positions of all the voxels of the construction space, respectively, and stores these data in the storage unit 190 (S50).

After step S50, the control unit 200 determines whether the calculation of data for all the projection directions is completed (S60). If at step S60 it is determined that the calculation of data for all the projection directions is not completed, the control unit 200 changes the irradiation position of the X-ray irradiator 110 through the drive unit 210 (S61). After the irradiation position of the X-ray irradiator 110 is changed at step S60, the control unit 200 obtains the transmission image of the subject 130, and repeats the above-described steps.

If at step S60 it is determined that the calculation of data for all the projection directions is completed, the control unit 200 constructs the three-dimensional image of the subject 130 on the basis of the data of all the voxels stored in the storage unit 190, and visually displays the three-dimensional image.

As described above, the present invention provides a three-dimensional image constructing method, in which a three-dimensional image can be constructed through an X-ray apparatus, thereby allowing a user to directly observe a subject and to precisely inspect the subject.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A three-dimensional image constructing method using an X-ray apparatus, said X-ray apparatus including an X-ray irradiator for irradiating X-rays to a subject, an image multiplier tube for causing an image to be formed thereon by X-rays having been transmitted through the subject, an image selection unit for selecting a specific region from the image multiplied by the image multiplier tube 140, and a photographing unit for obtaining the image of the specific region selected by the image multiplier tube, comprising:
   a setting step of setting a construction space of a subject and information for the construction space;
   an image obtaining step of obtaining a plurality of transmission images of the subject;
   an image processing step of calculating data of the construction space on the basis of the information for the construction space set at the setting step and the transmission images obtained at the image obtaining step; and
   a constructing step of constructing the construction space on the basis of the data calculated at the image processing step.

2. The three-dimensional image constructing method according to claim 1, wherein said setting step comprises steps of setting an irradiation position of the X-ray and a position at which the image is formed, and dividing a three-dimensional construction space desired to be constructed into a plurality of voxels and presetting positions of the voxels.

3. The three-dimensional image constructing method according to claim 2, wherein said image processing step comprises a space calculating step of calculating spatial densities of the voxels of the construction space on the basis of the irradiation position of the X-ray and the position at which the image is formed, and an applying step of applying the spatial densities to the voxels of the construction space.

4. The three-dimensional image constructing method according to claim 3, wherein said applying step is a step of setting the spatial densities at the positions of the voxels preset at the setting step.

5. The three-dimensional image constructing method according to claim 3, wherein values of said spatial densities are obtained from the following equation:

$$y^j = \sum_{i=1}^{N} a_i^j \cdot x_i$$

where i=an index for a voxel of an construction space, j=an index for an X-ray, a=a distance by which a jth X-ray is transmitted through an ith voxel, and $x_i$=a density value of an ith voxel.

6. The three-dimensional image constructing method according to claim 3, wherein distances by which all the X-rays are transmitted through all the voxels are obtained from the following equation:

$$Y = Ax,$$

and $$A = \begin{bmatrix} a_1^1 & a_2^1 & \cdots & a_N^1 \\ a_1^2 & a_2^2 & \cdots & a_N^2 \\ \cdots & \cdots & \cdots & \cdots \\ a_1^M & a_2^M & \cdots & a_N^M \end{bmatrix} = \begin{bmatrix} a^1 \\ a^2 \\ \cdots \\ a^M \end{bmatrix}$$

where M=the number of X-rays, and N=the number of voxels.

* * * * *